US010352315B2

(12) United States Patent
West (10) Patent No.: US 10,352,315 B2
(45) Date of Patent: Jul. 16, 2019

(54) AUTO LOADING AND UNLOADING PERISTALTIC PUMP APPARATUS

(71) Applicant: Fenwal, Inc., Lake Zurich, IL (US)

(72) Inventor: Richard L West, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 664 days.

(21) Appl. No.: 14/554,289

(22) Filed: Nov. 26, 2014

(65) Prior Publication Data

US 2016/0144090 A1     May 26, 2016

(51) Int. Cl.
| | |
|---|---|
| *F04B 43/12* | (2006.01) |
| *F04B 45/08* | (2006.01) |
| *A61M 1/10* | (2006.01) |

(52) U.S. Cl.
CPC ........... *F04B 43/12* (2013.01); *A61M 1/1039* (2014.02); *A61M 1/1001* (2014.02); *A61M 1/1006* (2014.02); *A61M 1/1043* (2014.02); *F04B 45/08* (2013.01)

(58) Field of Classification Search
CPC ................ A61M 1/1039; A61M 1/367; A61M 2205/12; F04B 43/12; F04B 43/1238; F04B 43/1246; F04B 43/1276; F04B 43/1292; F04B 43/1253; F04B 43/1284; F04B 45/08
USPC .............. 417/476, 477.2, 477.12, 477.3, 474
See application file for complete search history.

(56) References Cited

U.S. PATENT DOCUMENTS

| | | | | |
|---|---|---|---|---|
| 4,861,242 A | * | 8/1989 | Finsterwald | ........ F04B 43/1253 417/477.1 |
| 5,387,088 A | * | 2/1995 | Knapp | ................. F04B 43/1253 417/477.1 |
| 5,445,506 A | | 8/1995 | Afflerbaugh et al. | |
| 6,736,617 B2 | | 5/2004 | Domroese | |
| 7,547,200 B2 | | 6/2009 | O'Mahony et al. | |

FOREIGN PATENT DOCUMENTS

| | | |
|---|---|---|
| JP | 2005-74235 A | 3/2005 |
| WO | 1995/017603 A1 | 6/1995 |
| WO | 2007/038364 A2 | 4/2007 |
| WO | 2009/025686 A1 | 2/2009 |

OTHER PUBLICATIONS

International Preliminary Report on Patentability for Application No. PCT/US2015/062263, dated May 30, 2017, 7 pages.
The International Searching Authority, The International Search Report and Written Opinion for Intl. App. No. PCT/US2015/062263, dated Feb. 8, 2016.
Office Action for Japanese Patent Application No. 2017-528216, dated May 15, 2018, 9 pages (including translation).

* cited by examiner

*Primary Examiner* — Bryan M Lettman
(74) *Attorney, Agent, or Firm* — Cook Alex Ltd.

(57) ABSTRACT

A peristaltic pumping apparatus for use in blood processing procedures, comprising: a pump rotor rotatable about a rotational axis and a pump raceway circumferentially spaced about the axis; a pump cap disposed atop the pump rotor, the pump cap having a finger configured to engage a tubing loop of a length of tubing at a time of loading the tubing and guide the tubing loop within the raceway along the length of the tubing loop; and wherein the pump cap further comprises a tensioning wall disposed laterally opposite the finger, the tensioning wall configured to engage a length of the tubing loop at a time of unloading the tubing and provide tension to the tubing length as the tubing loop exits the raceway.

20 Claims, 8 Drawing Sheets

PRIOR ART

AUTO LOADING AND UNLOADING PERISTALTIC PUMP APPARATUS

CROSS-REFERENCE TO RELATED APPLICATIONS

This application claims the benefit of U.S. Non-Provisional patent application Ser. No. 14/554,289 filed Nov. 26, 2014, which is expressly incorporated herein by reference in its entirety.

FIELD OF THE DISCLOSURE

The present disclosure is directed to systems and methods for pumping fluid within flexible tubing. More particularly, the present disclosure is directed to systems and methods for peristaltic pumping of fluids used in connection with medical devices.

BACKGROUND

Roller or peristaltic pumps have many uses in the medical field. For example, roller pumps may be used in medical devices, such as automated apheresis and blood processing devices, to push fluid (e.g., blood or blood components) through flexible tubing. The operation of a roller pump is to pump fluid by positive displacement using revolving rollers that occlude the flexible tubing. Generally, roller pumps may be simply structured, generate a consistent flow, and use disposable tubing through which a fluid medium is transferred.

Roller pumps generally comprise a pump drive and a pump head. The pump drive causes rotation of the pump head to pump a fluid medium. The pump head often comprises a pump stator and a pump rotor. The pump stator may be a chamber or housing having an inner circumferential surface (or "raceway") against which one or more tubes are compressed by the pump rotor. The pump rotor, which may be rotatable relative to the stator and raceway, may be arranged in the pump stator in such a manner that the pump rotor engages tubing loops positioned in the pump stator with one or more rollers. Upon rotation of the pump rotor by a rotating shaft that is otherwise part of the pump drive, the roller(s) may compress the tubing loop against the inner circumferential surface of the pump stator as it is rolled along the tubing. The fluid medium contained in the tubing may then be transported in a direction of the pump rotor rotation.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

According to an exemplary embodiment, the present disclosure is directed to a peristaltic pumping apparatus for use in blood processing procedures, comprising a pump rotor rotatable about a rotational axis and a pump raceway circumferentially spaced about the axis; a pump cap disposed atop the pump rotor, the pump cap having a finger configured to engage a tubing loop of a length of tubing at a time of loading the tubing and guide the tubing loop within the raceway along the length of the tubing loop; and wherein the pump cap further comprises a tensioning wall disposed laterally opposite the finger, the tensioning wall configured to engage a length of the tubing loop at a time of unloading the tubing and provide tension to the tubing length as the tubing loop exits the raceway.

According to an exemplary embodiment, the present disclosure is directed to a method for loading and unloading a pump tubing loop into and out of a pump raceway, the method comprising: placing in the vicinity of a pump raceway a flexible tubing loop of a length of tubing; engaging the tubing loop with a finger of a pump cap positioned atop a pump rotor and guiding the tubing loop within the raceway along a length of the tubing loop with the finger, wherein the pump rotor is rotatable about a rotational axis and the pump raceway is circumferentially spaced about the axis; and unloading from the pump raceway the flexible tubing loop, wherein a tensioning wall disposed laterally opposite the finger engages a length of the tubing loop and provides tension to the tubing length as the tubing loop exits the raceway.

According to an exemplary embodiment, the present disclosure is directed to a peristaltic pumping apparatus for use in a medical device, comprising a pump rotor rotatable about a rotational axis and a pump raceway circumferentially spaced about the axis. The apparatus also comprises a pump cap disposed atop the pump rotor, the pump cap having a finger configured to engage a tubing loop of a length of tubing at a time of loading the tubing and guide the tubing loop within the raceway along the length of the tubing loop. The pump cap further comprises a tensioning wall disposed laterally opposite the finger, the tensioning wall configured to engage a length of the tubing loop at a time of unloading the tubing and provide tension to the tubing length as the tubing loop exits the raceway. The finger extends radially outward from the rotational axis of the pump rotor beyond a circumference of the pump rotor and the tensioning wall has a contour that generally follows the circumference of the pump rotor.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Some embodiments may minimize tangling, bunching, and/or folding of pump tubing loops during the loading or unloading of the tubing loops into and out of the raceway.

Some embodiments may enable automatic loading of pump tubing loops into the pump raceway prior to a medical procedure and automatically unload pump tubing loops out of the pump raceway upon completion of the procedure.

Some embodiments may minimize loading and unloading issues with both shorter and longer tubing loops.

Some embodiments may minimize loading and unloading issues with both faster and slower pump rotational speeds.

Some embodiments may minimize loading and unloading issues with both faster and slower speeds with which a cassette is loaded and unloaded.

Figure 1:
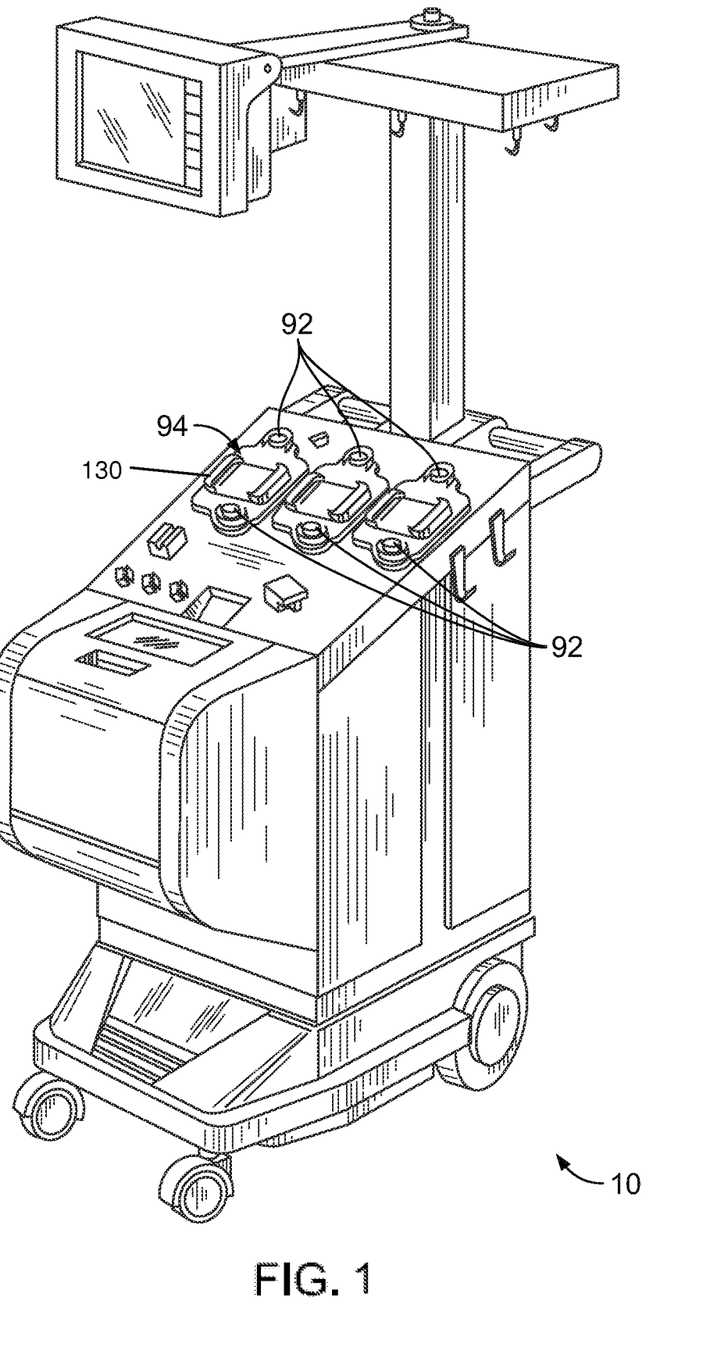
FIG. 1 is a perspective view of a fluid processing system incorporating a peristaltic pumping apparatus, according to an exemplary embodiment.
Figure 2:
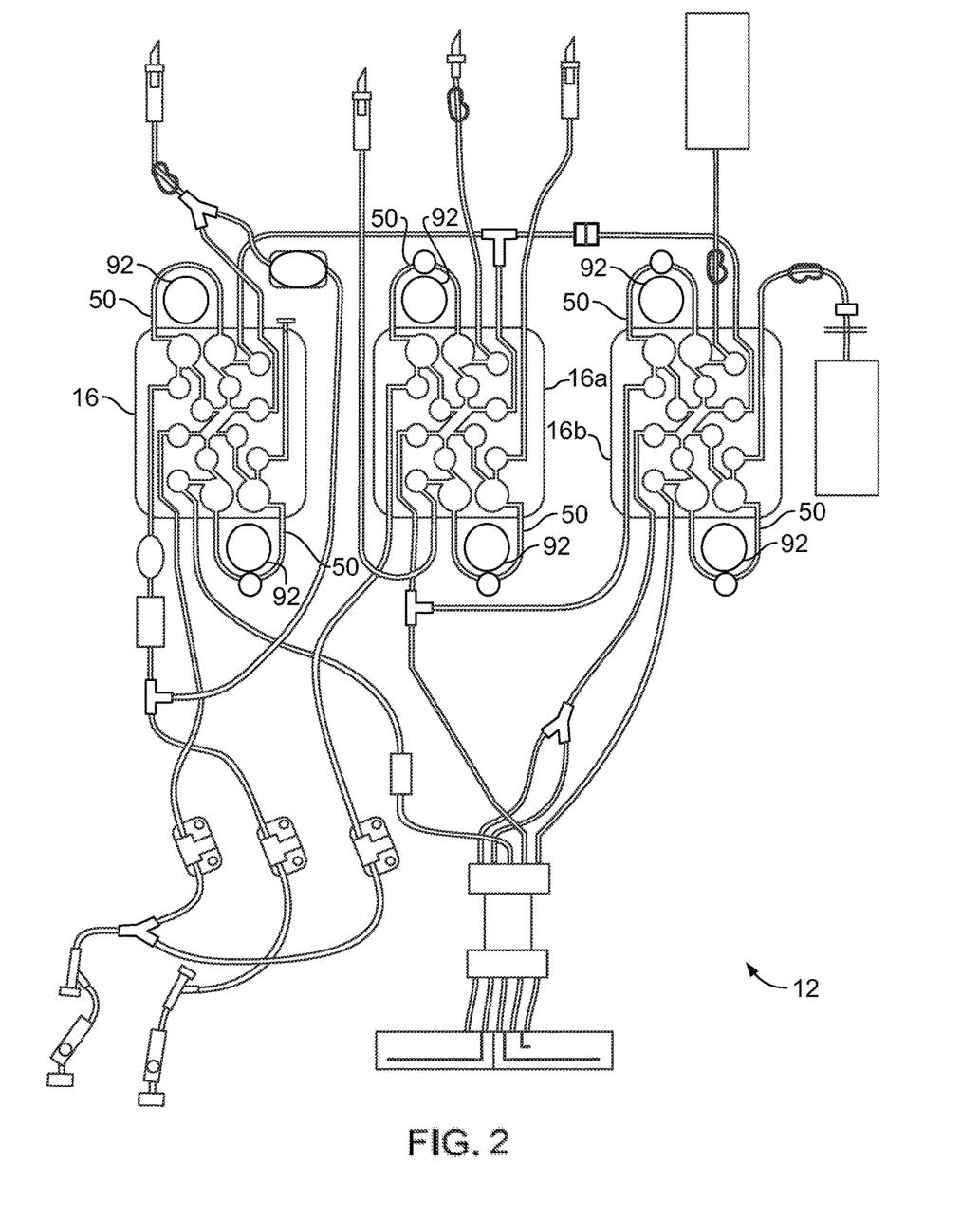
FIG. 2 is a diagrammatic view of a disposable fluid circuit and cassette that may be used in combination with the fluid processing system of FIG. 1, according to an exemplary embodiment.

FIG. 1 shows an exemplary fluid processing system 10 incorporating a peristaltic pumping apparatus 92 used in conjunction with a disposable fluid circuit 12 (FIG. 2). The fluid processing system 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety, although any suitable apheresis device or blood processing system may be used. The system 10 can be used for processing various fluids, including, but not limited to whole blood, blood components, or other suspensions of biological cellular materials. While an improved pumping apparatus 92 will be described herein with reference to exemplary system 10 and disposable fluid circuit 12, it should be understood that these principles may be employed with other fluid processing systems and disposable fluid circuits without departing from the scope of the present disclosure.

Figure 3:
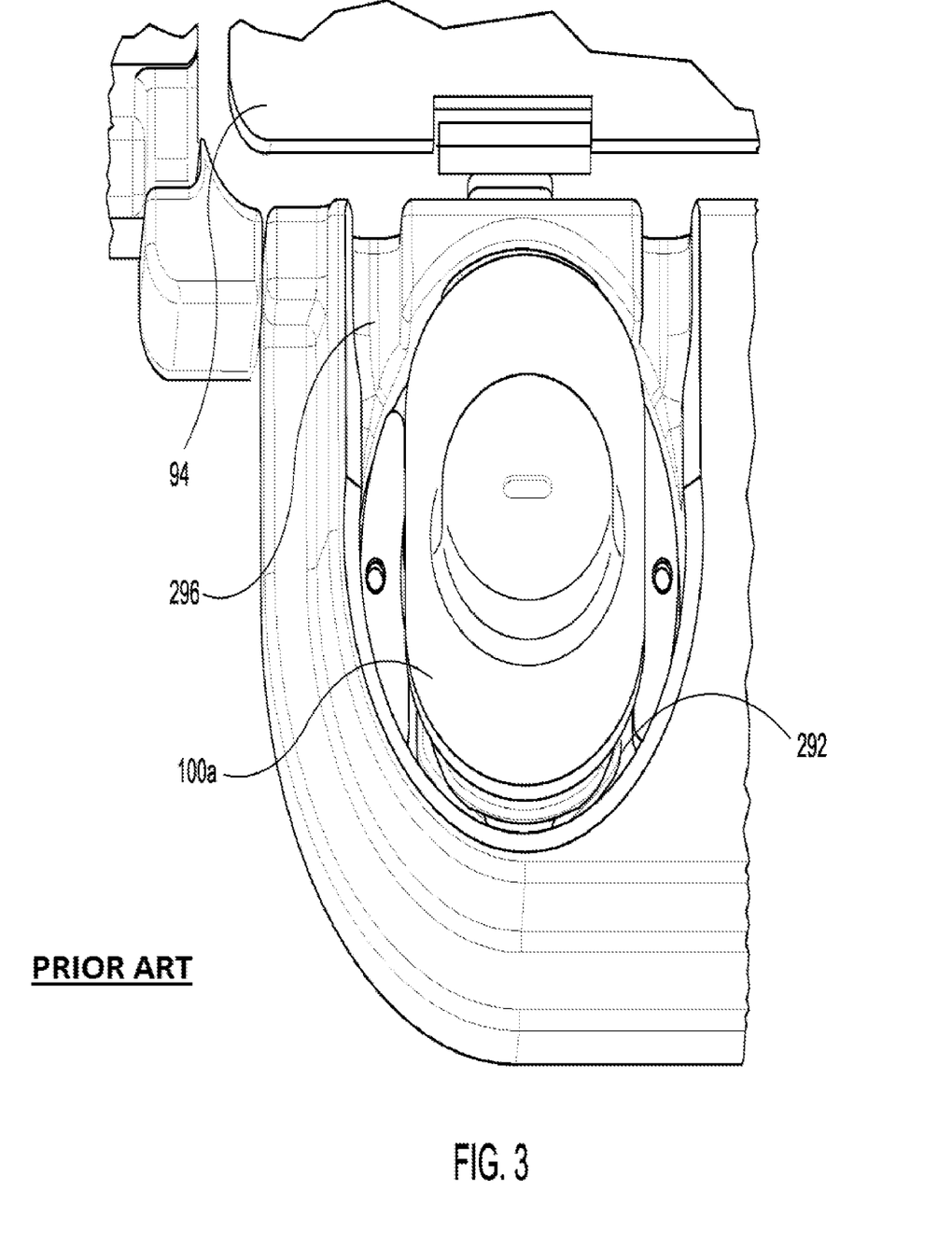
FIG. 3 is a perspective view of a pump cap known in the art, according to an exemplary embodiment.

Fluid entering the disposable fluid circuit 12 may be pumped thereinto by one or more pumps 92 of the fluid processing system 10 acting upon one or more of the flexible tubing loops 50 extending from the cassettes 16, 16a, and 16b of the flow circuit 12. The tubing loop 50 may be in an erect and outwardly bowed position from cassette 16, 16a, and 16b. An exemplary cassette 16, exemplary pump mechanism, and associated cassette holders 94 are described in greater detail in U.S. Pat. No. 5,480,294, which is hereby incorporated herein by reference in its entirety, although any suitable cassette, pump mechanism, and cassette holder may be used. The pump mechanism may optionally be equipped with a pump cap, such as pump cap 100a that is known in the art, depicted in FIG. 3. The contour of known pump cap 100a generally conforms to the circumference of the underlying rotor of the pump mechanism and may play a role in protecting the rotor and pump mechanism.

Turning to the cassette holders 94 in FIG. 1, each may receive and grip one of the cassettes 16, 16a, and 16b along the two opposed sides edges 130 in the desired operating position. The cassette holder 94 may include a pair of peristaltic pump apparatuses 92. When the cassette 16 is gripped by the cassette holder 94, tubing loops 50 extending from the cassette 16 as shown in FIG. 2 may make operative engagement with the pump apparatuses 92. The pump apparatuses 92 may be operated to cause fluid flow through the cassette 16. Although the embodiment in FIG. 1 depicts three cassette holders 94 configured to engage tubing loops 50 of the fluid circuit 12, any number of cassette holders 94 may be incorporated into the fluid processing system 10. Although FIG. 1 also depicts peristaltic pump apparatuses 92 disposed on laterally opposing sides of cassette holders 94, the pump apparatuses 92 may be oriented in a variety of configurations depending on the orientation and number of the tubing loops 50 extending from cassettes 16, 16a, and 16b.

Figure 3A:
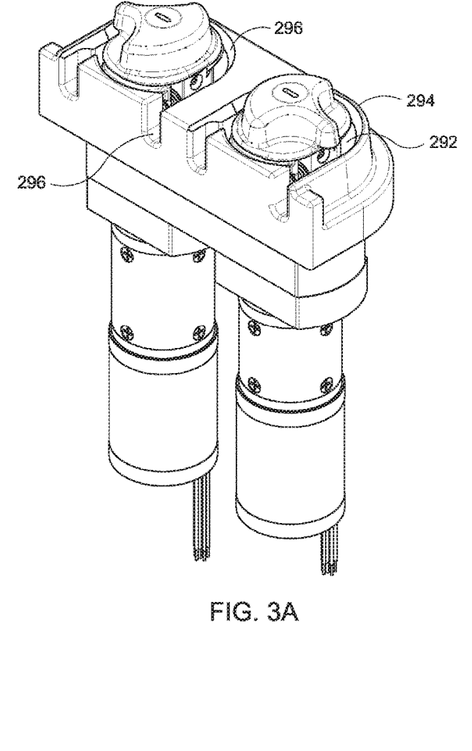
FIG. 3A is a perspective view of a pump apparatus, according to an exemplary embodiment.
Figure 3B:
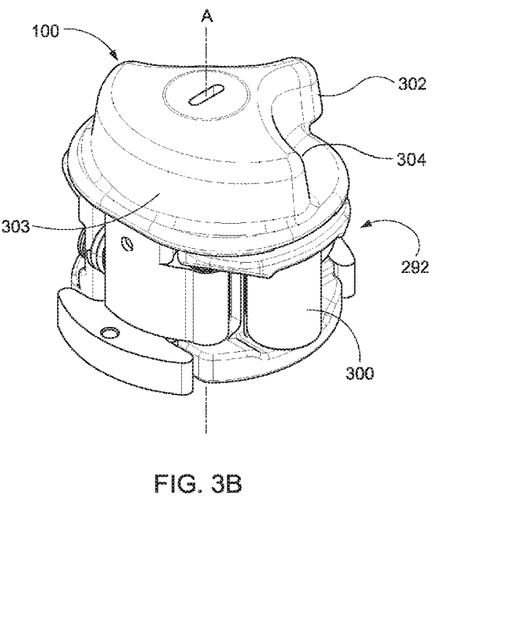
FIG. 3B is a perspective view of a pump rotor assembly and pump cap, according to an exemplary embodiment.

Turning to FIGS. 3A and 3B, detailed views of the pump apparatus 92 are shown. The pump apparatus 92 may comprise a pump rotor assembly 292 rotatable about a rotational axis A. An outer wall 294 may extend at least partially around the back side of each rotor assembly 292. The space between the outer wall 294 and the rotor assembly 292 forms a pump raceway 296 circumferentially spaced about the axis A. When a cassette 16, 16a, and 16b is gripped by the side edges 130, the tubing loops 50 may extend into the pump raceway 296. Loading a cassette 16 and tubing loop 50 may be performed by the side edges 130 moving the tubing loop 50 and cassette 16 toward the pump rotor in a direction generally parallel to the rotational axis A of the pump rotor. Unloading a cassette 16 and tubing loop 50 may be performed by the side edges 130 moving the tubing loop 50 and cassette 16 away from the pump rotor in a direction generally parallel to the rotational axis A. Each rotor assembly 292 may include a set of diametrically spaced rollers 300, although the spacing of one or more rollers 300 may be varied. In use, as the pump rotor 292 rotates, the rollers 300 in succession may compress the associated tubing loop 50 against the outer wall 294 of the pump raceway 296. This peristaltic pumping action may urge fluid through the associated loop 50.

Each rotor assembly 292 may have a pump cap 100 capping the assembly 292. The pump cap 100 may comprise a tensioning finger 302, which may extend radially outwards from the rotational axis A of the pump rotor assembly 292 and beyond the circumference of the rotor assembly 292. The tensioning finger 302 may be disposed above the height of the rotor assembly 292 and the raceway 296 and may facilitate the smooth loading of the tubing loop 50 into the raceway 296 by catching and guiding the tubing loop 50 in place into the raceway 296. The tensioning finger 302 may assure that the tubing loops 50 are properly oriented and aligned within their respective pump races 296 so that the desired peristaltic pumping action occurs.

The pump cap 100 of the rotor assembly 292 may also comprise a tensioning wall 303 disposed laterally opposite the tensioning finger 302 and also above the height of the rotor assembly 292 and the raceway 296. The contour of the tensioning wall 303 may generally follow the circumference of the rotor assembly 292. The tensioning wall 303 may facilitate the smooth unloading of the tubing loop 50 out of the raceway 296 by preventing slack in the tubing loop 50 during unloading and providing tension to the tubing loop 50 as it exits the raceway 296. Providing tension to the tubing loop 50 may minimize the tubing loop 50 from bending and folding over itself during the unload process. The pump cap 100 of the rotor assembly 292 may also comprise a bottom lip 304 (FIG. 3B) extending from the tensioning wall 303 at a nonparallel angle to the tensioning wall 303. In one embodiment, the bottom lip 304 may comprise an upper flat surface 305 upon which the tubing loop 50 may rest to prevent downward slippage of the tubing loop 50 during loading and/or unloading, thereby allowing the tensioning wall 303 to maximize grasp of the tubing loop 50. The upper flat surface 305 of the bottom lip 304 may extend radially outwards beyond the tensioning wall 303. In one embodiment, the upper flat surface 305 may extend radially outwards beyond the tensioning wall 303 but not radially beyond the pump rotor.

At least one transitional wall 304 (FIG. 3B) extends between the tensioning finger 302 and the tensioning wall 303 of the pump cap 100. At least a portion of the at least one transitional wall 304 extends radially outward from the rotational axis A to a lesser extent than at least a portion of the tensioning finger 302 and at least a portion of the tensioning wall 303.

Figure 4A:
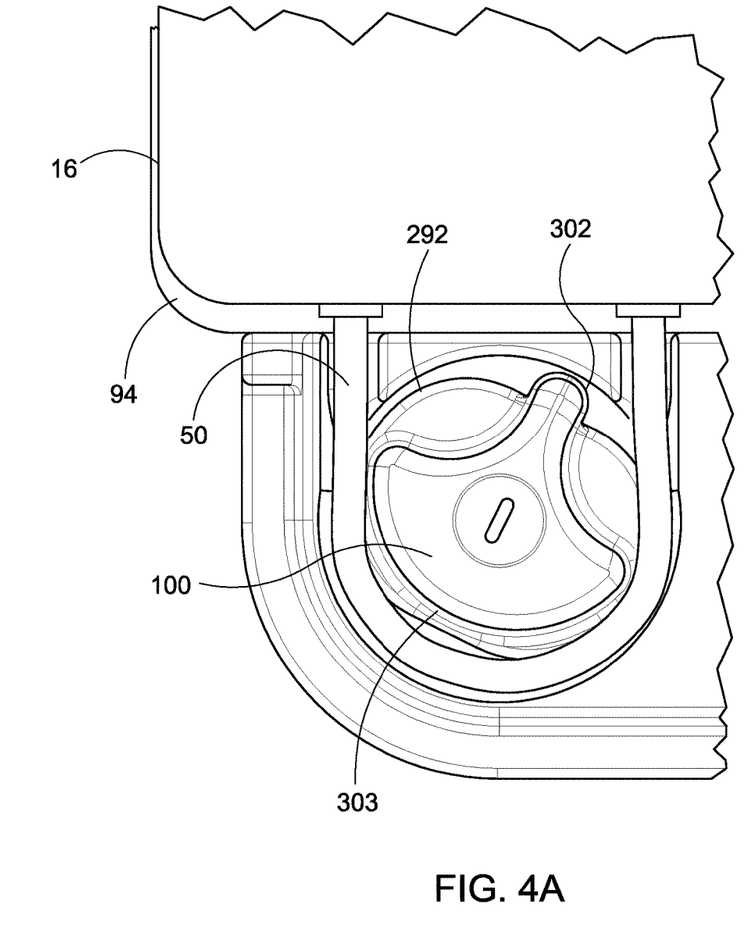
FIGS. 4A-4C are perspective views of a cassette and associated tubing loop at various points of loading, according to an exemplary embodiment.

FIG. 4A depicts a cassette 16 and associated tubing loop 50 just prior to being loaded into the raceway 296. The tubing loop 50 is disposed in the vicinity of the raceway 296 at the height of the pump cap 100 above the raceway 296 and generally above the rotor assembly 292. The pump rotor 292 may begin rotating about its rotational axis A prior to the tubing loop 50 having settled within the raceway 296.

Figure 4B:
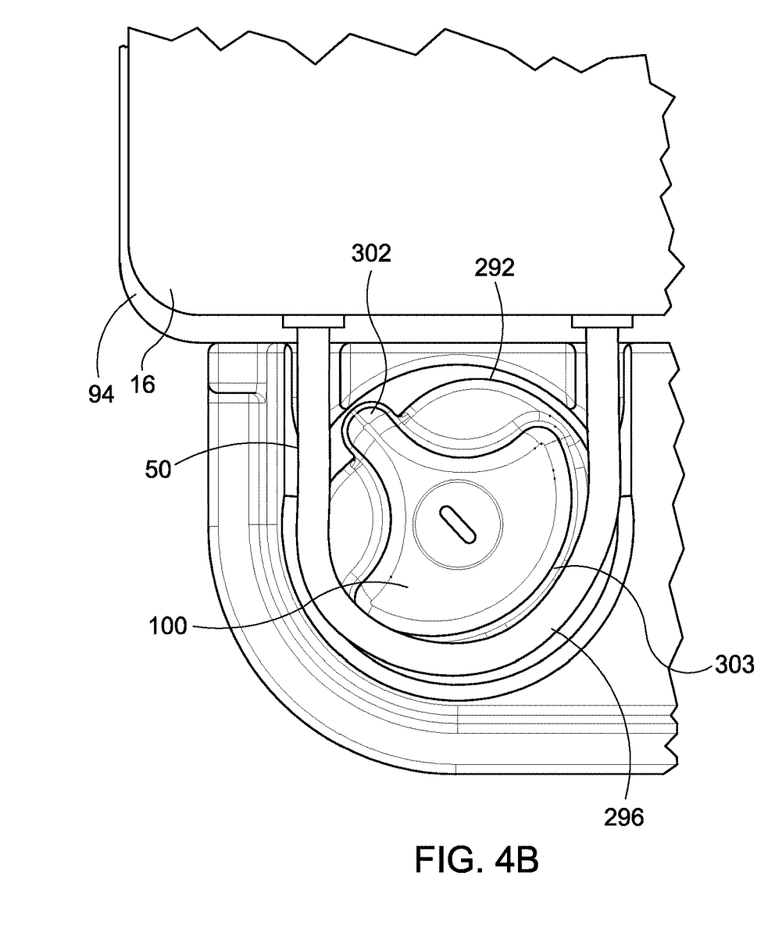

Turning to FIG. 4B, as the side edges 130 of the cassette holders 94 load the cassette 16 into the cassette holders 94, the tubing loop 50 may begin loading into the raceway 296 around the rotor assembly 292, starting with the portions of the tubing loop 50 closest to the cassette 16. The portion of the tubing loop 50 distal from the cassette 16 may still be unloaded and may straddle a portion of the pump cap 100.

Figure 4C:
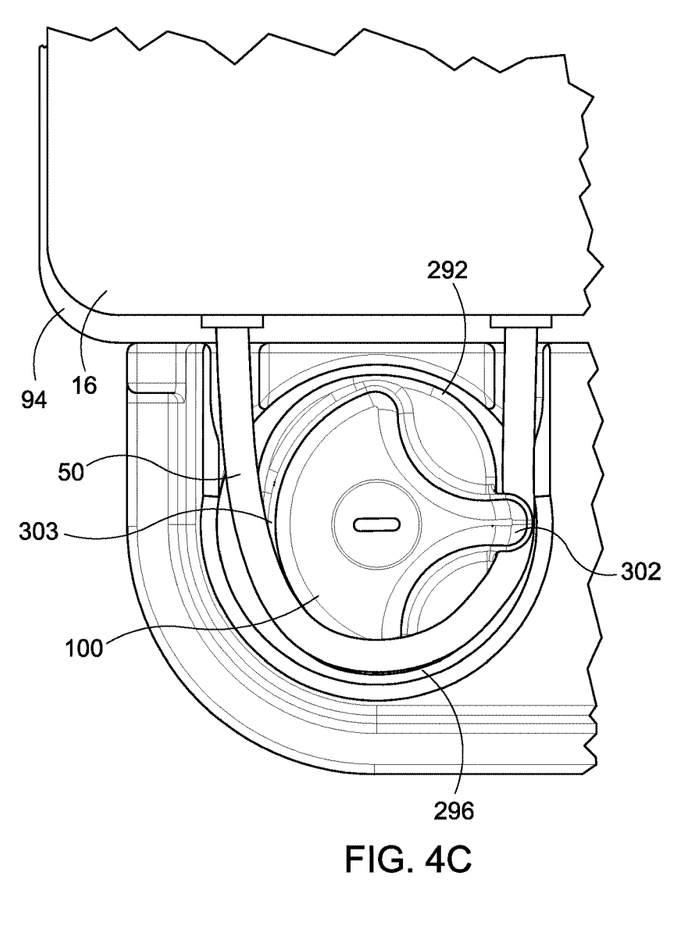

Referring to FIG. 4C, the rotation of the pump rotor 292 about its rotational axis A allows the finger 302 to catch the tubing loop 50 such that a portion of the loop 50 proximal to the cassette 16 is caught underneath the finger 302. The finger 302 may guide the tubing loop 50 along its length into the raceway 296. The finger 302 may take one or more rotations of the pump rotor 292 to guide the tubing loop 50 completely into the raceway 296. It may take more rotations of the finger 302 to guide the tubing loop 50 completely info the raceway 296 in cases where the tubing loop 50 is shorter. Once the tubing loop 50 has been fully loaded into the raceway 296, the rollers 300 of the rotating pump rotor 292 may facilitate transport of fluid along the tubing loop 50.

Figure 5A:
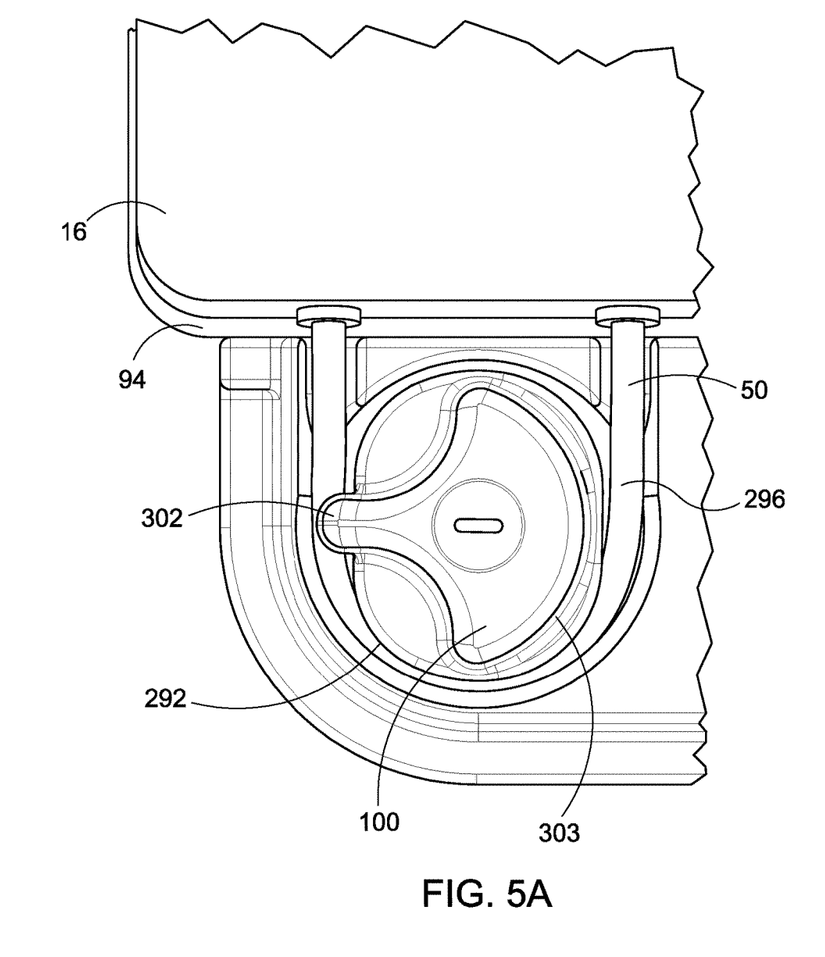
FIGS. 5A-5C are perspective views of a cassette and associated tubing loop at various points of unloading, according to an exemplary embodiment.

FIG. 5A shows an embodiment in which the cassette 16 is loaded into the cassette holders 94 and has just commenced the unloading process. As the side edges 130 elevate the cassette 16 into an unloading position, portions of the tubing loop 50 most proximal to the cassette 16 may first exit the raceway 296. The pump rotor 292 and hence the pump cap 100 may continue to rotate during the unloading process.

Figure 5B:
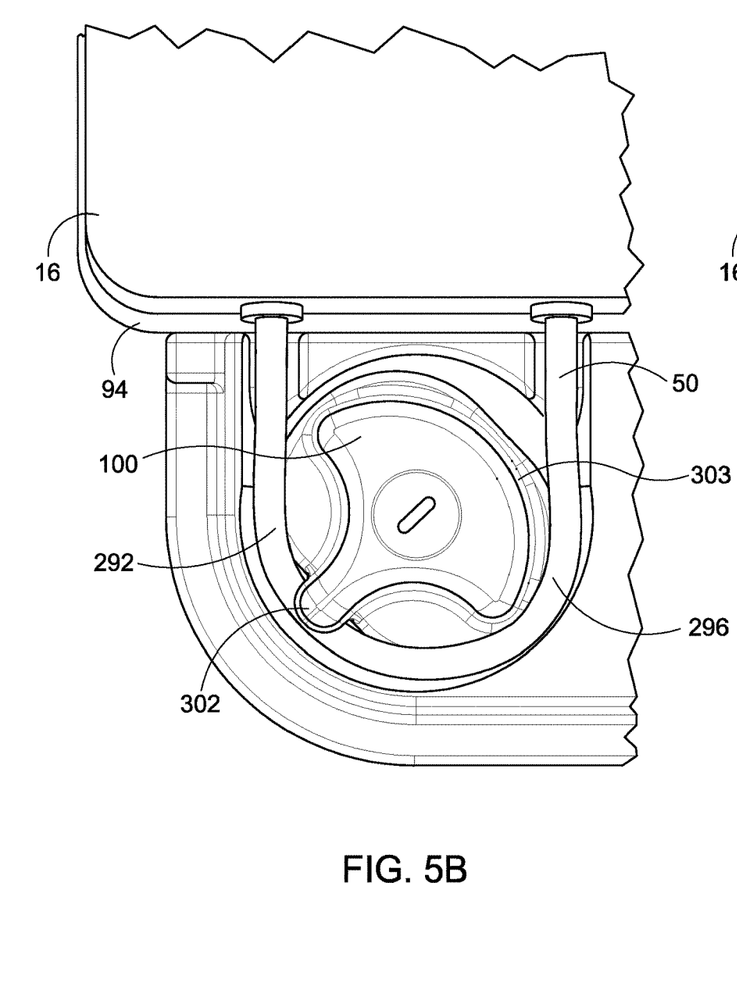
Figure 5C:
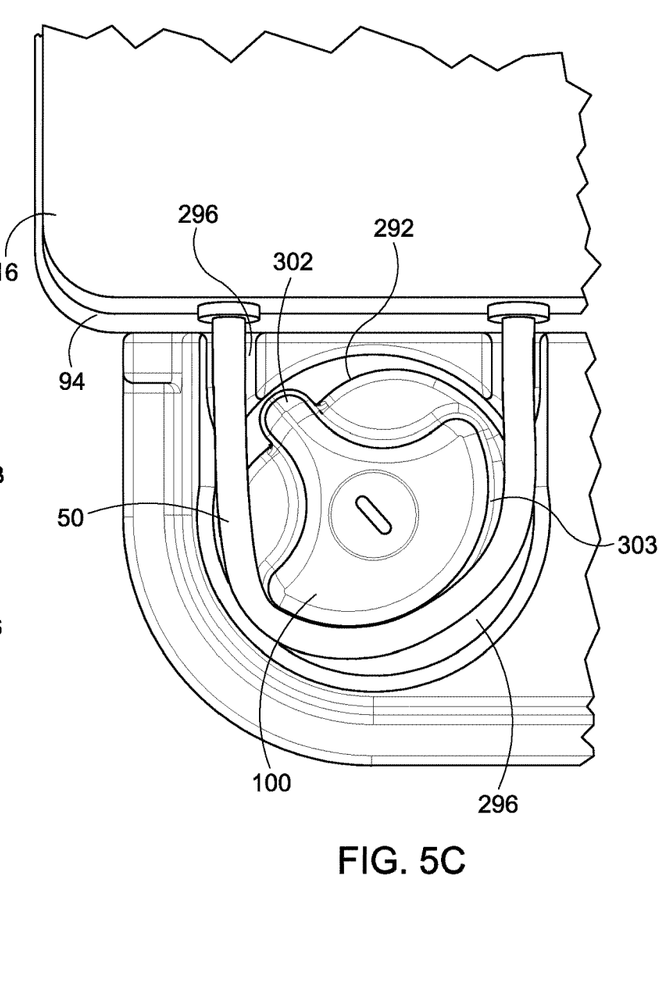

Referring to FIG. 5B, as portions of the tubing loop 50 more distal to the cassette 16 continue to exit the raceway 296, the tensioning wail 303 may progressively make more contact with the tubing loop 50. The tensioning wall 303 may create tension along the length of tubing loop 50 so as to avoid slack and therefore minimize portions of the tubing 50 bending and folding over itself as well as to expedite the exit of all portions of the tubing loop 50 from the raceway 296. FIG. 5C shows a point at which the entire tubing loop 50 has exited the raceway 296. The tensioning wail 303 may hold a length of the tubing loop 50 taut so that loop 50 does not fall back into the raceway 296. The tensioning wall 303 may therefore allow the fluid processing system 10 and pumping apparatus 92 to accommodate tubing loops of shorter and longer lengths.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A peristaltic pumping apparatus for use in blood processing procedures, comprising:
   a pump rotor having a rotor circumference and rotatable about a rotational axis;
   a pump raceway circumferentially spaced about the rotational axis;
   a tubing loop; and
   a pump cap disposed atop the pump rotor, the pump cap having
      a finger configured to engage the tubing loop when in an unloaded state of the tubing loop and guide at least a portion of the tubing loop within the raceway along a length of said at least a portion of the tubing loop, with a distal-most portion of the tubing loop being configured to extend radially outward from the rotational axis beyond the finger of the pump cap when in the unloaded state,
      a tensioning wall disposed opposite the finger with respect to the rotational axis, the tensioning wall forming a single, continuous, elongated, arcuate surface configured to engage the tubing loop when in the unloaded state of the tubing loop and provide tension to the length of said at least a portion of the tubing loop as the tubing loop exits the raceway, wherein the tensioning wall is co-planar with the finger and has an arcuate extent about the rotational axis greater than an arcuate extent of a radially outermost end of the finger, and
      at least one transitional wall extending between the finger and the tensioning wall, wherein at least a portion of said at least one transitional wall extends radially outward from the rotational axis to a lesser extent than at least a portion of the finger and at least a portion of the tensioning wall.

2. The peristaltic pumping apparatus of claim 1, wherein the pump rotor includes a set of diametrically spaced rollers.

3. The peristaltic pumping apparatus of claim 1, wherein the finger extends radially outward from the rotational axis of the pump rotor beyond the circumference of the pump rotor.

4. The peristaltic pumping apparatus of claim 1, wherein the raceway comprises a space between the pump rotor and an outer wall extending at least partially around a back side of the pump rotor.

5. The peristaltic pumping apparatus of claim 1, wherein said at least a portion of the tubing loop is configured to be loaded into the pump raceway by moving the tubing loop toward the pump rotor in a direction substantially parallel to the rotational axis of the pump rotor.

6. The peristaltic pumping apparatus of claim 1, wherein at least a portion of the finger and/or at least a portion of the tensioning wall is disposed above the pump rotor and the raceway.

7. The peristaltic pumping apparatus of claim 1, wherein the tensioning wall is configured to progressively make more contact with the tubing loop as the tubing loop exits the raceway.

8. The peristaltic pumping apparatus of claim 1, wherein the pump cap further comprises a bottom lip extending from the tensioning wall, wherein a flat portion of the bottom lip extends radially outwards beyond the tensioning wall.

9. A method for loading and unloading at least a portion of a tubing loop into and out of a pump raceway circumferentially spaced about a pump rotor having a rotational axis, the method comprising:

placing a tubing loop in the vicinity of the pump raceway;
engaging the tubing loop with a finger of a pump cap positioned atop the pump rotor, wherein prior to engaging the tubing loop, a distal-most portion of the tubing loop extends radially outward beyond a radially outermost end of the finger of the pump cap;
guiding at least a portion of the tubing loop within the pump raceway using the finger; and
unloading the tubing loop from the pump raceway, with a tensioning wall of the pump cap disposed opposite the finger with respect to the rotational axis engaging the tubing loop and providing tension to a length of said at least a portion of the tubing loop as the tubing loop exits the raceway, wherein
the tensioning wall forms a single, continuous, elongated, arcuate surface co-planar with the finger and having an arcuate extent about the rotational axis greater than said radially outermost end of the finger, and
at least one transitional wall extending between the finger and the tensioning wall, wherein at least a portion of said at least one transitional wall extends radially outward from the rotational axis to a lesser extent than at least a portion of the finger and at least a portion of the tensioning wall.

10. The method of claim 9, wherein the pump rotor includes a set of diametrically spaced rollers.

11. The method of claim 9, wherein the finger extends radially outward from the rotational axis of the pump rotor beyond a circumference of the pump rotor.

12. The method of claim 9, wherein the tensioning wall is configured to prevent slack in the tubing loop during unloading.

13. The method of claim 9, wherein the raceway comprises a space between the pump rotor and an outer wall extending at least partially around a back side of the pump rotor.

14. The method of claim 9, wherein said at least a portion of the tubing loop is configured to be loaded into the pump raceway by moving the tubing loop toward the pump rotor in a direction substantially parallel to the rotational axis of the pump rotor.

15. The method of claim 9, wherein at least a portion of the finger and/or at least a portion of the tensioning wall is disposed above the pump rotor and the raceway.

16. The method of claim 9, wherein the pump cap further comprises a bottom lip extending from the tensioning wall, wherein a flat portion of the bottom lip extends radially outwards beyond the tensioning wall.

17. A peristaltic pumping apparatus for use in a medical device, comprising:
a pump rotor having a rotor circumference and rotatable about a rotational axis;
a pump raceway circumferentially spaced about the rotational axis; and
a pump cap disposed atop the pump rotor, the pump cap having
a finger configured to engage and guide at least a portion of a tubing loop at a time of loading said at least a portion of the tubing within the raceway along a length of said at least a portion of the tubing loop, with the finger including a radially outermost end configured to be positioned radially inwardly of a distal-most portion of the tubing loop with respect to the rotational axis prior to the time of loading,
a tensioning wall disposed opposite the finger with respect to the rotational axis, the tensioning wall forming a single, continuous, elongated, arcuate surface configured to engage the tubing loop at a time of unloading said at least a portion of the tubing loop and provide tension to the length of said at least a portion of the tubing loop as the tubing loop exits the raceway, wherein the tensioning wall is co-planar with the finger and has an arcuate extent about the rotational axis greater than an arcuate extent of said radially outermost end of the finger, and
at least one transitional wall extending between the finger and the tensioning wall, wherein at least a portion of said at least one transitional wall extends radially outward from the rotational axis to a lesser extent than at least a portion of the finger and at least a portion of the tensioning wall.

18. The peristaltic pumping apparatus of claim 17, wherein the raceway comprises a space between the pump rotor and an outer wall extending at least partially around a back side of the pump rotor.

19. The peristaltic pumping apparatus of claim 17, wherein the tensioning wall is configured to progressively make more contact with the tubing loop as the tubing loop exits the raceway.

20. The peristaltic pumping apparatus of claim 17, wherein the pump cap further comprises a bottom lip extending from the tensioning wall, wherein a flat portion of the bottom lip extends radially outwards beyond the tensioning wall.

* * * * *